(12) United States Patent
Liu et al.

(10) Patent No.: US 6,168,941 B1
(45) Date of Patent: Jan. 2, 2001

(54) METHOD OF PRODUCING ADENOVIRAL VECTOR STOCKS

(75) Inventors: Lee-Cheng Liu, Columbia; Shoupeng Lai, Burtonsville, both of MD (US)

(73) Assignee: GenVec, Inc., Gaithersburg, MD (US)

( * ) Notice: Under 35 U.S.C. 154(b), the term of this patent shall be extended for 0 days.

(21) Appl. No.: 09/545,385

(22) Filed: Apr. 7, 2000

(51) Int. Cl.$^7$ .................................................. C12N 7/00
(52) U.S. Cl. ............................................. 435/235.1
(58) Field of Search ........................................... 435/235.1

(56) References Cited

U.S. PATENT DOCUMENTS

| | | | |
|---|---|---|---|
| 4,117,881 | 10/1978 | Williams et al. | 435/1.3 |
| 4,304,293 | 12/1981 | Scheiwe et al. | 165/247 |
| 4,327,799 | 5/1982 | Scheiwe et al. | 165/263 |
| 4,377,077 | 3/1983 | Granlund | 62/457.1 |
| 4,455,842 | 6/1984 | Granlund | 62/64 |
| 4,676,070 | 6/1987 | Linner | 62/115 |
| 5,994,134 | 11/1999 | Giroux et al. | 435/403 |

FOREIGN PATENT DOCUMENTS

WO 00/32754 A1   6/2000  (WO).

OTHER PUBLICATIONS

Brunner et al., *Gene Therapy*, 7, 401–407 (2000).
Chillakuru et al., *Biotechnol. Prog.*, 7, 85–92 (1991).
Côté et al., *Biotechnology and Bioengineering*, 59 (5), 567–575 (1998).
Côté et al., *Biotechnol. Prog.*, 13, 709–714 (1997).
Garnier et al., *Cytotechnology*, 15, 145–155 (1994).
Green et al., *Virology*, 20, 199–207 (1963).
Kamen et al., *Biotechnology and Bioengineering*, 50 (1), 36–48 (1996).
Le Doux et al., *Biotechnology and Bioengineering*, 63 (6), 664–652 (1999).
Nadeau et al., *Biotechnology and Bioengineering*, 51, 613–623 (1996).
Spector et al., in *Cells: A Laboratory Manual*, vol. 1, 2.11–2.13 (Cold Spring Harbor Laboratory Press, Dec. 1997).

*Primary Examiner*—Robert A. Schwartzman
*Assistant Examiner*—Andrea Ousley
(74) *Attorney, Agent, or Firm*—Leydig, Voit & Mayer, Ltd.

(57) ABSTRACT

The present invention provides a method of producing an adenoviral vector stock by providing a culture of cells permissive for growth of adenoviral vectors, wherein the cells are in a medium, culturing the culture under conditions to permit growth of the cells, perfusing fresh medium through the culture for a period of about 1–6 hours, in an amount of at least about two times the volume of medium in the culture, while the density of the cells in the medium is about 40–70% of the density of cells obtained in the medium when the growth of the culture is in the stationary phase, contacting the culture with adenoviral vectors under conditions permissive for the infection of the cells after the perfusion of fresh medium is substantially completed, culturing the infected cells to replicate the adenoviral vectors, and harvesting the infected cells to obtain an adenoviral vector stock.

20 Claims, No Drawings

METHOD OF PRODUCING ADENOVIRAL VECTOR STOCKS

TECHNICAL FIELD OF THE INVENTION

This invention pertains to the production of viral vector stocks.

BACKGROUND OF THE INVENTION

Modified viruses, also known as viral vectors, have proven convenient vector systems for investigative and therapeutic gene transfer applications, and adenoviral vector systems present several advantages for such uses. Due to these advantages, researchers have developed numerous gene therapy applications based upon adenoviral vectors. As such adenoviral vector based applications move through clinical trials and into approved medical applications, there will be an increasing need for efficient large-scale production of adenoviral vector stocks.

Systems for production of virus stocks in cell cultures are known in the art. Several references in the prior art teach general methods for the production of virus stocks in cell cultures (see, e.g., U.S. Pat. Nos. 4,055,466, 4,072,565, and 4,080,258). Due to the variations in stock production amongst the wide variety of viral vectors and cell types permissive for growth thereof, generalized methods have often proven unsuitable for large-scale production of viral vector stocks, particularly stocks of recombinant viral vectors.

More recently, researchers have studied the production of recombinant viral vector stocks by focussing on specific types of viral vectors. For example, systems drawn to production of recombinant baculovirus stocks in insect cells have been extensively researched (see, e.g., Kamen et al., *Biotechnology and Bioengineering*, 50(1), 36–48 (1996)). Other researchers have studied systems for the production of recombinant retroviruses (see, e.g., Le Doux et al., *Biotechnology and Bioengineering*, 63(6), 664–652 (1999)). The adsorption and replication rates of Vaccinia virus in batch cultures has also been previously studied (see Chillakuru et al., *Biotechnol. Prog.*, 7, 85–92 (1991)).

In comparison to the procedures available to produce baculovirus and other non-adenoviral vector stocks, relatively few systems for production of adenoviral vector stocks are known. U.S. Pat. No. 5,994,134 teaches the use of a microcarrier-based bioreactor process for producing viruses in cells at high densities, including adenoviruses, in serum-based medium. The limitations attendant serum-based mediums and microcarrier bioreactors limit the applicability of this method. Garnier et al., *Cytotechnology*, 15, 145–55 (1994), provides a method of producing high levels of recombinant proteins in 293 cells infected with recombinant adenoviral vectors by infecting the cells at various concentrations in combination with single or double medium replacements post infection. Furthering this research, Côté et al., *Biotechnology and Bioengineering*, 59(5), 567–75 (1998), teaches production of recombinant proteins in adenoviral vector-infected 293 cells at cell densities of up to $1 \times 10^7$ cells/ml. However, neither Garnier et al. nor Côté et al. addresses the production of adenoviral vector stocks.

Accordingly, there is a need for alternative methods of producing adenoviral vector stocks. The present invention provides such methods. This and other advantages of the present invention, as well as additional inventive features, will be apparent from the description of the invention provided herein.

BRIEF SUMMARY OF THE INVENTION

The present invention provides a method of producing an adenoviral vector stock. The steps of the method include providing a culture of cells permissive for growth of adenoviral vectors, wherein the cells are in a medium, culturing the culture under conditions to permit growth of the cells, perfusing fresh medium through the culture, in an amount of at least about two times the volume of medium in the culture, while the density of the cells in the medium is about 40–70% of the density of cells obtained in the medium when the growth of the culture is in the stationary phase, contacting the culture with adenoviral vectors under conditions permissive for the infection of the cells after the perfusion of fresh medium is substantially completed, culturing the infected cells to replicate the adenoviral vectors, and harvesting the infected cells to obtain an adenoviral vector stock.

DETAILED DESCRIPTION OF THE INVENTION

The present invention provides a method of producing an adenoviral vector stock. The steps of the method include (a) providing a culture of cells permissive for growth of adenoviral vectors, wherein the cells are in a medium, (b) culturing the culture under conditions to permit growth of the cells, (c) perfusing fresh medium through the culture for a period of about 1–6 hours, in an amount of at least about two times the volume of medium in the culture, while the density of the cells in the medium is about 40–70% of the density of cells obtained in the medium when the growth of the culture is in the stationary phase (also referred to as the "stationary phase density"), (d) contacting the culture with adenoviral vectors under conditions permissive for the infection of the cells after the perfusion of fresh medium in step (c) is substantially completed, (e) culturing the infected cells to replicate the adenoviral vectors, and (f) harvesting the infected cells to obtain an adenoviral vector stock.

The cells can be any suitable type of cells for producing an adenoviral vector stock. Thus, any cells that are capable of acting as adenoviral vector producing cells are suitable. Examples of suitable cells include cells of primary cell lines, such as human embryonic kidney (HEK), human embryonic lung (HEL), and human embryonic retinoblast (HER) cells, although other cells (e.g., HELA cells or cultured tissue cells) can be suitable. Preferably, the cells are, or are derived from, anchorage dependent cells, but which have the capacity to grow in suspension cultures. Preferred HEK cells are 293 cells, and cells from cell lines which are derived from 293 cells. Preferred HEL cells are A549 cells, and cells from cell lines derivative thereof.

Preferably, the cells are modified to contain DNA corresponding to, or derived from, some portion (e.g., one or more nucleotide sequences) of the adenoviral genome so as to be capable of complementing an adenoviral vector deficient in such sequences, particularly a replication-deficient adenoviral vector such as are generally described in U.S. Pat. No. 5,994,106 and International Patent Application WO 95/34671. More preferably, the cell is capable of such complementation of the adenoviral vector, while preventing homologous recombination between the adenoviral vector and complementing cell.

Preferably, the modified cells are of, or derived from, 293, A549 or modified HER cells. Modified HER cells, in particular offer several advantages over other cells capable of producing adenoviral vector stocks. Thus, it is desirable, for example, that such modified HER cells are highly transfectable, exhibit much lower frequencies of homologous recombination as 293 cells, and, when infected with adenoviral vectors, are associated with the appearance of plaques in monolayers of the cells in about 3–4 days (versus, for example, 6–10 days associated with 293 cells). Thus, such modified HER cells when infected with adenoviral vectors enable faster performance of plaque assays, than, for example, 293 cells. More desirably, the HER cells are associated with yields of adenoviral vectors at higher rates than in other cell types, more preferably at rates of about 2–3 times as high as those achieved with 293 cells infected with similar adenoviral vectors. Examples of suitable modified HER cells include 911 cells, described in Fallaux et al., *Human Gene Therapy*, 7, 215–222 (1996). Particularly preferred modified HER cells are PER.C6 cells (Introgene, Inc.), which are described in International Patent Application WO 97/00326.

The cells form a culture, which is maintained in a suitable medium. The culture of cells can be any suitable culture for the production of adenoviral vector stocks where fresh medium can be perfused through the culture, in an amount of at least about two times the volume of medium prior to such perfusion. Examples of suitable cultures include perfusion cultures, substrate-supported cultures, microcarrier-supported cultures, fluid bed cultures, or suspension cultures. Preferably, the culture is either a perfusion cell culture, such as a continuous-perfusion cell culture, or a suspension culture, such as suspension cultures used in roller bottle cultures and suspension bioreactor cultures. Such cultures are well known and commonly used in the art. Suspension cultures are particularly favored, most preferably when such cultures are maintained in a batch or fed-batch mode before and after perfusion of the fresh medium through the culture.

The culture is in a medium. The medium can be any suitable medium for maintaining the cells and permitting the propagation of adenoviral vectors therein. Numerous examples of mediums suitable for use in the practice of the present invention, and the principles to generate modified or new suitable mediums, are widely known in the art. In general, the medium will contain a selection of secreted cellular proteins, diffusable nutrients, amino acids, organic and inorganic salts, vitamins, trace metals, sugars, and lipids as well as perhaps other compounds such as growth promoting substances (e.g., cytokines). The medium should be suitable for growth of the cell type that is utilized to produce the adenoviral vector stock, and will thus mimic physiological solutions and conditions (e.g., pH) under which such cells naturally flourish. Numerous commercial cell and medium combinations are available and one of ordinary skill will readily be able to determine the desired conditions for the culture.

Both undefined and defined mediums can be suitable mediums in the context of the present invention. An undefined medium is a medium in which the specific contents of the medium (e.g., content and quantities of proteins and nutrients) are not known or specified by a set regimen. Examples of suitable undefined mediums include mediums based on animal serum, such as fetal bovine serum (e.g.) (FBS), or which utilize an alternative nutritional source, for example enzymatic digestions of meat, organs or glands, as well as milk or hydrolysates of wheat gluten. When an undefined medium is used in the context of the present invention, it is preferred that the medium be a serum free medium (SFM). SFM does not contain serum but still can contain animal-derived components, e.g., albumin, fetuin, hormones, as well as "undefined" components, such as organ extracts.

More preferably, the medium used in the context of the present invention is a defined medium. A defined medium is a medium wherein the contents of the medium are known and/or set to a specific regimen. A defined medium typically is formulated to meet the needs of specific cell types. One example of a defined medium is a basal medium. A basal medium is generally composed of vitamins, amino acids, organic and inorganic salts, and buffers. Additional "defined" components, such as bovine serum albumin (BSA), can be added to make a basal medium more nutritionally complex. Suitable defined mediums include protein-free and protein-containing mediums. Preferably, where a defined medium is used an animal protein-free medium is used. An animal protein-free medium can contain proteins but does not contain proteins that are of animal origin. A particularly preferred medium is an animal protein-free medium, which contains recombinant proteins and growth factors (e.g., epidermal growth factor (EGF) and insulin-like growth factor (IGF)), as well as lipids (e.g., cod liver extracts) and cholesterol. An example of a commercially available preferred medium is Ex-Cell 525 (JRH Biosciences). It is also desirable that such media are supplemented with glutamine.

The culture can be prepared in any suitable manner, which will allow the growth and sustenance of adenoviral vector producer cells. Typically, the medium will be inoculated with the cells, which are typically contained in a storage culture, such as a viable frozen cell culture, to produce the culture. If the cell-containing culture is contained as a frozen cell culture, it is desirable to subject the cells to freezing under conditions suitable for maintaining a high percentage of viable cells in the culture for future use. Several methods of freezing cells for future use are known in the art. However, the ability of such methods to maintain high percentages of viable cells in the culture for use after storage widely varies. A particularly favored method of preserving a viable cell-containing medium (e.g., a cell culture) comprises (a) providing a viable cell-containing medium, (b) reducing the temperature of the viable cell-containing medium by about 1.5° C./minute from about 4° C. or higher to about −40° C., (c) maintaining the temperature of the viable cell-containing medium at about −40° C. for a period of time of about one minute or longer, (d) reducing the temperature of the viable cell-containing medium to a temperature of about −150° C. or lower (for example, by immersing the viable cell-containing medium in liquid nitrogen ($LN_2$)), and (e) maintaining the viable cell-containing medium at a temperature of about −150° C. or lower. Preferably, the temperature of the culture is lowered to about −180° C. or lower, or even more preferably to about −195° C. or lower. The period of time the cell culture is held at about −40° C. can be any time period of about one minute or longer. The use of this method of preserving cells results in improved retention of the percentage of viable cells during storage and upon thawing over other protocols which rely on immersion in $LN_2$ for freezing cells. Other advantages of the described method are that the addition of potentially contaminating, or perhaps even toxic, cryoprotectants is not required, nor is the addition of energy during the freezing process to retain cell viability, or the use of vacuums.

When the frozen cell culture is desired for use, it is thawed to a suitable temperature. Any suitable thawing technique can be used, and several are known in the art. For example, the cell-containing culture can be subjected to a "quick thaw" by placing the culture in an appropriate container and subjecting the container (and culture therein) to a 37° C. $H_2O$ bath while shaking the container rapidly in the bath until the culture is approximately ¾ thawed, with a small portion of the culture still frozen. At this point, the culture is removed from the H$_2$O bath, but shaking is continued until the culture has thawed completely. After thawing, the frozen-cell culture is ready for continued culturing. Preferably, such frozen cell cultures are used as an inoculate for a culture including, or consisting of, fresh medium.

After inoculation with the cells, the culture is then "cultured" or cultivated under conditions to permit growth of the cells. Any suitable manner of culturing the culture that permits the growth of the adenoviral vector producing cells is suitable in the context of the present invention. The method of culturing such cells will depend upon the type of adenoviral vector cell selected. Suitable culturing methods are well known in the art, and typically involve maintaining pH and temperature within ranges suitable for growth of the cells. Preferred temperatures for culturing are about 35–40° C., more preferably about 36–38° C., and optimally about 37° C. Preferably, the pH of the culture is maintained at about 6–8, more preferably at about 6.7–7.8, and optimally at about 6.9–7.5.

From inoculation of the culture and during the cultivation of the culture, the growth of the cells typically will follow a characteristic pattern composed of five stages. The first stage, or lag phase, occurs at the introduction of cells or storage culture into the medium to form the culture. Preferably, the cells or storage culture (i.e., the "inoculum") used to inoculate the medium will be composed of a high percentage of viable cells and a relatively fresh storage medium in order to reduce the length of the lag phase.

The lag phase is typically followed by a log (or exponential) phase, in which cells divide at the maximum possible growth rate, thus increasing the number of total viable cells in the culture. The cell growth rate is dependent on the growth medium and growth conditions (e.g., aeration, pH level etc.), which are preferably optimized to promote cell growth during the log phase. However, under no condition will cell growth rate surpass the maximum doubling time which itself is dependent upon cell type. The cell growth rate during the exponential phase is constant, but because each cell divides at a slightly different moment the growth curve rises gradually. The log phase is followed by a decelerating phase, where the rate of increase in viable cells in the culture decreases. The decelerating phase is followed by a stationary phase where the total number of viable cells in the culture does not increase any more, an effect caused either by a lack of cell division or by a balanced ratio of cell division and cell death. If the cell culture is not harvested before or during the stationary phase, the culture moves through a second decelerating phase, wherein total numbers of viable cells decline, followed by an exponential death phase. Cell density increases throughout the growth cycle of the culture. The concentration of the cells in the medium can be monitored while culturing the culture.

Cell growth rates, and thus the above-described growth cycle, can be determined by numerous techniques well known in the art. Techniques focusing on total number of cells in the culture include determining the weight of the culture, assessing culture turbidity, determining metabolic activity in the culture, electronic cell counting, microscopic cell counting of culture samples, plate counting using serial dilutions, membrane filter counting, and radioisotope assays. Mechanical systems for measuring cell density, based upon these and other principles and particularly suited for use in bioreactors, are reviewed in, for example, Junker et al., *Bioprocess Engineering*, 10, 195–207 (1994). More recently, mass spectrometry and other advanced analytical techniques have been used in a similar fashion (see, e.g., Behrendt et al., *Cytotechnology*, 14, 157–65 (1994)). In the context of the present invention, any technique permissive for assessing cell density is suitable. Cell density of a culture can be determined spectrophotometrically or by using a counting chamber, such as a hemocytometer. Preferably, a hemocytometer is used. In brief, hemocytometer-based techniques involve taking a sample of the culture, counting (and possibly also examining) a statistically significant number of cells in a given space in the hemocytometer, and determining the density of cells in the culture using simple mathematical formulas.

Cell viability also can be determined by a number of techniques known in the art. A preferred technique is the dye exclusion technique, which utilizes an indicator dye to identify cell membrane damage. Cells which absorb the dye become stained and are considered non-viable. Dyes such as trypan blue, erythrosin, and nigrosin are commonly used. Preferably, trypan blue based assays are used. Further details of performing such methods and other cell culturing and analysis methods are provided in, for example, Lubiniecki, *Large-Scale Mammalian Cell Culture Technology* (Marcel Dekker, Inc., New York, 1990), Kostaninov et al., *Trends in Biotechnol.*, 12, 324–33 (1994), Mather, "Making Informed Choices: Medium, Serum, and Serum-Free Medium", Chapter 2 in *Methods in Cell Biology*, 57, 19–30 (1998), Freshney, *Culture of Animal Cells* (Alan R. Liss, Inc., 1987), Harrison, *General Techniques of Cell Culture* (Cambridge Univ. Press 1997), *Animal Cell Culture Methods*, Barnes and Mather (eds.) (1998), and Bonarius et al., *Biotechnology and Bioengineering*, 45, 524–35 (995).

The culture is cultured until the density of the cells in the medium is about 40–70% (e.g., about 45–70% or even about 50–70%) of the density of cells which would be (or will be) obtained in the medium when the growth of the culture is in the stationary phase. While the culture is within this range of cell density, fresh medium is perfused through the culture for about 1–6 hours in an amount of at least about two times the volume of the medium in the culture at that time (i.e., immediately prior to such perfusion). This high volume perfusion over a short time may be referred to as "intense perfusion", and serves both to provide fresh medium and to remove substantial amounts of spent medium accumulated in the culture prior to the initiation of the intense perfusion. More preferably, fresh medium in an amount of about three to four times the volume of the culture is perfused through the culture. Even more fresh medium may be perfused through the culture, but an amount of about three to four times the volume of the medium in the culture is most preferred, particularly in view of the cost attendant perfusion with fresh medium and the lack of significant increases in adenoviral vectors produced by perfusion with additional medium.

Perfusion through the culture means that a certain volume of medium is added to the culture and a substantially identical amount of medium is removed from the culture without removing a significant percentage of the cells in the culture. The intense perfusion can be carried out by any suitable technique. Typically, a bioreactor with perfusion capabilities is used to accomplish such perfusion. For continuous perfusion cultures, perfusion of fresh medium is taking place throughout culturing; however, the continuous perfusion rate is altered as necessary to ensure that fresh medium is perfused through the culture in an amount of at least about two times the volume of the medium in the culture, when the cell density in the culture is at the values described herein. Typically, for continuous perfusion cultures, perfusion through the culture occurs at a rate of about 1–4 volumes of medium in the culture per day. While continuous culturing is a suitable means for adding fresh medium to the culture to sustain the cells during culturing, it is not effective in removing large amounts (e.g., over about 20%, 50%, 65%, or even higher percentages) of the spent medium from the culture.

The perfusion of the at least about two times the volume of the medium in the culture can occur at any suitable rate, such that the intense perfusion is completed in about 1–6 hours. In particular, suitable rates are rates where fresh medium is added quickly enough to provide fresh medium to the culture over a short period of time, but slow enough such that the shear rate in the culture does not result in loss of large percentages of viable cells in the culture due to shear. Perfusion rates during the intense perfusion will depend on the type of system used to perfuse medium through the culture (e.g., the type of pump used to perfuse the medium). Several suitable perfusion systems are known, and the ordinarily skilled artisan will readily be able to determine an appropriate rate for the particular system used. Preferably, the intense perfusion will occur at a rate such that the intense perfusion takes about 2–4 hours, and, even more preferably, about 2–3 hours. Perfusion through the culture during the intense perfusion occurs at a rate of about 70–200% of the volume of the medium in the culture per hour. More preferably the rate is at about 80–150% of the volume of the medium in the culture per hour. Perfusion rates of about 1.3 volumes of the medium in the culture per hour during the intense perfusion step in a 10 liter bioreactor are particularly preferred.

By perfusing fresh medium through the culture in an amount of at least about two times the volume of the culture, about 66% or more of the spent media is removed from the culture (and replaced with fresh medium) prior to contact with the adenoviral vectors. For example, intense perfusion of fresh medium in an amount equal to about three to four times the volume of the culture results in about 95% or more of the spent medium in the culture being removed (and thus replaced with fresh medium). An advantage of adding at least about 66% fresh medium to the culture by the perfusion of at least about two times the volume of medium of the culture through the culture is that nutrient "starvation" of the cells in the culture, and consequent lower percentage of viable cells in the culture, are avoided. Accordingly, such levels of medium exchange are preferred. While some spent medium remains in the culture, such low levels of spent medium in the culture during and after infection with the adenoviral vectors does not significantly impact adenoviral vector yield. Thus, continuous perfusion techniques or perfusion of fresh medium at higher levels prior to contacting the culture with the adenoviral vectors is less desirable.

Preferably, the fresh medium is perfused through the culture while the density of the cells is about 44% to about 70% (e.g., about 44–63%), more preferably about 55–70% (e.g., about 60–70%) of the density of the culture at the stationary phase, even more preferably while the density of cells is about 62–69% (e.g., about 65%) of the density of the culture at the stationary phase. Typically, such densities are achieved during the mid-to-late exponential phase of the culture.

The actual density of cells in the medium at stationary phase can be any suitable density. The specific stationary phase density for any culture will depend upon the specific components of the culture (e.g., type of cells and medium used), and will depend significantly on the type, and size, of culture. Typical stationary phase density can be $1-9 \times 10^6$ cells/ml. For example, for a 10 liter fed-batch or batch bioreactor of a HER cell culture, stationary phase density is typically about $1.5 \times 10^6 - 2.6 \times 10^6$ cells/ml, more typically about $1.5 \times 10^6 - 2 \times 10^6$ cells/ml. For 10 liter continuous perfusion bioreactors, the stationary phase density often is higher, such as $5-6 \times 10^6$ cells/ml for A549 cells in a 10 liter continuous perfusion bioreactor. In contrast, for 293 cells and cells of 293-derived cell lines, as well as HER cell lines, grown in a 10 liter continuous perfusion bioreactor, typical stationary stage cell density will be about $7-9 \times 10^6$ cells/ml. As 10 liter fed batch, batch, and continuous perfusion cultures are preferred, these cell densities represent preferred stationary phase cell densities in the practice of the invention. The number of cells in the medium when the culture is in the stationary phase can be determined by allowing some portion of the culture to progress to stationary phase or by assessing substantially similar cultures wherein the density of the culture at the stationary phase is determined.

The density of cells in the medium during the intense perfusion typically is about $0.8-4.2 \times 10^6$ cells/ml. In particular, the density of cells in the medium during the intense perfusion typically is $0.8 \times 10^6 - 1.1 \times 10^6$ cells/ml, more specifically about $1.0 \times 10^6 - 1.1 \times 10^6$ cells/ml, in 10 liter fed batch and batch bioreactors. In a 10 liter fed-batch bioreactor, cell densities while the fresh medium is perfused through the culture can be about $0.8 \times 10^6 - 1.4 \times 10^6$ cells/ml, more specifically about $1.1 \times 10^6 - 1.3 \times 10^6$ cells/ml. For a 10 liter continuous perfusion bioreactor such densities will be about $2.4 \times 10^6 - 4.2 \times 10^6$ cells/ml. Such densities represent preferred densities at which the fresh medium should be perfused through the culture in an amount of at least about two times the volume of the medium in the culture.

The time to reach the cell density when the fresh medium will be perfused through the culture in an amount of at least two times the volume of the medium in the culture will vary depending upon the vector, type of cells, and type of culture used during the cell growth cycle. For example, starting with frozen cells with a density of less than $3 \times 10^5$ cells/ml., a period of about 6–10 days may be required to achieve the aforementioned cell densities. The culture can be grown in a single container or in multiple containers. For example, the culture can be grown initially in multiple roller bottles, until a desired cell density is achieved, then the separated culture can be unified in a single container, such as a bioreactor, or in different bioreactors.

Besides direct measurement or monitoring of the cell density, one of ordinary skill in the art will be able to determine times or other indications that correspond to the aforementioned cell densities for the cells and culture used to produce the adenoviral vector stocks. Thus, for example, a time corresponding to the cell density associated with optimal stock production can be determined for a particular stock and selected as an indicator of when the culture should be contacted with the adenoviral vectors in practicing the invention with a substantially similar stock (e.g., same cell type and same medium). Another technique that is available is the use of mathematical growth formulas, based on one or more sample points during the growth of the culture, such as the Monrod Model. Either type of technique, or other similar techniques, can be combined with mechanical monitoring techniques or other techniques for practicing the invention under such determined parameters.

When one of the aforementioned cell densities or other appropriate indications are reached, and the intense perfusion of fresh medium through the culture is substantially completed, preferably entirely completed, the culture is contacted with adenoviral vectors under conditions permissive for infection of the cells. Preferably, such contact of the culture with the adenoviral vectors occurs very near to the completion of such perfusion of fresh medium through the culture, and ideally the contact occurs simultaneously with the completion of such perfusion. Because the fresh medium is perfused through the culture, the density of the culture will remain significantly unchanged by the intense perfusion of such fresh medium (ideally the cell densities in the culture before and after such perfusion are equal). Therefore, the aforementioned cell densities used to indicate when perfusion of fresh medium through the culture is appropriate also are indicative of cell densities when the culture should be contacted with the adenoviral vectors. Any suitable cell density within about 40–70% of the stationary phase density is suitable, and preferred ranges for contacting and infecting the cells with the adenoviral vectors are substantially identical to the aforementioned preferred ranges for performing the intense perfusion. Preferred cell densities for a particular cell type suitable for production of an adenoviral vector stock may vary somewhat within the range of 40–70% of the stationary phase density based on the particular cell type. Suitable densities allow for the production of high yields of assembled adenoviral vectors, particularly active/viable adenoviral vectors, in contrast to the mere production of proteins by the infected cells, which typically is associated with infecting cells at cell densities well above 70% of the stationary phase density.

The adenoviral vector can be any adenoviral vector capable of growth in an cell, which is in some significant part (although not necessarily substantially) derived from or based upon the genome of an adenovirus. Adenoviral vectors are well known in the art, and are characterized in, for example, U.S. Pat. Nos. 5,559,099, 5,712,136, 5,731,190, 5,837,511, 5,846,782, 5,962,311, 5,965,541, 5,981,225, 5,994,106, 6,020,191, and Thomas Shenk, "Adenoviridae and their Replication", and M. S. Horwitz, "Adenoviruses", Chapters 67 and 68, respectively, in *Virology*, B. N. Fields et al., eds., (3rd ed.), Raven Press, Ltd., New York, 1996. The adenoviral vectors can be based on the genome of any suitable wild-type adenovirus. Preferably, the adenoviral vectors are derived from the genome of a wild-type adenovirus of subgroup C, especially of serotype 5 (Ad5).

The adenoviral vectors can be replication deficient. Replication deficient adenoviral vectors are well known in the art and are described, for example, in U.S. Pat. No. 5,994, 106 as well as the aforementioned references. The adenoviral vector can be a multiply deficient adenoviral vector, such as described in U.S. Pat. No. 5,851,806 and International Patent Application WO 95/34671. Replication deficient adenoviral vectors require growth in either a complementary cell line or in the presence of a helper virus, which provides, in trans, the essential functions absent from the deficient vector (Berker et al., *J. Virol.*, 61, 1213–1220 (1987); Davidson et al., *J. Virol.*, 61, 1226–1239 (1987); Mansour et al., *Mol. Cell Biol.*, 6: 2684–2694 (1986)). Preferably, as mentioned above, the cells used to propagate replication deficient adenoviral vectors are complimentary cell lines and which allow replication of the adenoviral vector due to the ability of such cells to express gene products lacking in the replication deficient adenoviral vector.

Some of the adenoviral vectors can be adenoviral gene transfer vectors. Preferably, the adenoviral vectors consist essentially of adenoviral gene transfer vectors and more preferably all of the adenoviral vectors are adenoviral gene transfer vectors. An adenoviral gene transfer vector is an adenoviral vector capable of introducing one or more exogenous genes into a cellular environment, and more preferably is a vector capable of expressing one or more such exogenous genes. The production of adenoviral gene transfer vectors is well known in the art, and involves using standard molecular biological techniques such as those described in, for example, Maniatis et al., *Molecular Cloning: A Laboratory Manual*, (2d ed.), Cold Spring Harbor Press (1992), Watson et al., *Recombinant DNA*, (2d ed.), Scientific American Books (1992), Ausubel et al., *Current Protocols in Molecular Biology* (1987), and in several of the aforementioned references. Preferably, the exogenous gene will be a component of an expression cassette including one or more regulatory sequences (e.g., a promoter and/or enhancer sequence, such as a cytomegalovirus (CMV) promoter), and termination and/or mRNA poly adenylation (polyA) coding sequence, and will code for an expressible polypeptide or mRNA (e.g., a therapeutic protein).

Upon and after contact of the culture with the adenoviral vectors, the adenoviral vectors are permitted to infect the cells. Conditions for adenoviral vector infection are well known in the art and are described in several of the aforementioned references. The temperature of the culture during contact of the culture with the adenoviral vectors is preferably about 35–40° C., more preferably about 36–38° C., and optimally about 37° C. The pH during contact of the culture with the adenoviral vectors is preferably about 6.7–7.8, more preferably about 6.9–7.5. While the contact between the adenoviral vectors and the culture can be performed at any suitable concentration (such as by concentrating the medium up to $5 \times 10^6$ cells/ml or even higher), the culture can be, and preferably is, contacted with the adenoviral vectors without concentrating the cells prior to such contact. The ratio of adenoviral vectors contacting with the culture to the cells in the culture (otherwise known as the multiplicity of infection or MOI) desirably is greater than one, and more preferably is about five or higher.

The contact of the adenoviral vectors under conditions permissive for infection can be performed for any suitable period of time which enables a desired level of infection of the cells with the adenoviral vectors. The time for infection will depend at least on the titer of the virus and the specific cell type employed (because some cell types may have a greater density of the receptor which adenovirus uses to attach to cells) and the available surface area available to the adenoviral vectors (which is a function of the culture type and/or the cell type employed). Additionally the desired period of time can be affected by the type of adenoviral vector utilized (e.g., the virus can have an altered coat protein through recombinant engineering or be conjugated with a chemical entity, that affects its ability to bind to cells). One of ordinary skill in the art can readily determine an appropriate period of time for contact of the culture with the adenoviral vectors by taking such variables into account. Typically, a period of about one hour is sufficient under most conditions for infection by adenoviral vectors based on serotype 5, although longer periods (e.g., at least about 2, 3, 5, 10, 15, or 24 hours, or even longer) can be used. Typically, the period of contact of the cells with the adenoviral vector, and the period of culture of the cells after such contact, are contemporaneous, as the culture is not concentrated and no medium exchange or other significant modification to the culture occurs after contacting the culture with the adenoviral vectors.

Medium exchange during contact of the culture with the adenoviral vectors is not necessary, and, preferably, the perfusion of the fresh medium through the culture prior to infection is the only medium exchange used throughout the process of producing the adenoviral vector stock. Similarly, it is preferred that other nutritional supplements are not added after infection (e.g., glucose). Medium exchange during or soon after contacting the culture with the adenoviral vector can result in the undesired removal of viable adenoviral vectors from the medium after their introduction to the culture. If, however, medium exchange is performed after infection, preferably less than 100% of the medium is exchanged, more preferably about 50% or less of the medium is exchanged. Furthermore, as stated above, the cells can be contacted with the adenoviral vectors without concentrating the cells prior to and/or during such contact. Preferably, particularly for large scale production of adenoviral vector stocks, the culture is not significantly concentrated before perfusion of the fresh medium or during the contact of the culture with the adenoviral vectors and, most preferably, is not concentrated at all. The avoidance of concentrating the culture during the production of the adenoviral vectors is desirable inasmuch as the concentration process can involve the need for large and expensive equipment (e.g., a centrifuge capable of concentrating a 10 liter culture) and intensive labor.

After contacting the culture with the adenoviral vectors under conditions permissive for infection of the cells, the infected cells are then cultured to complete production of the adenoviral vector stock. Similarly to culturing the cells prior to contact, the infected culture can be cultured under any suitable conditions permissive for the propagation of the adenoviral vectors within the cells. Preferably, the pH of the culture is maintained at about 6.5–7.5, more preferably at about 6.9–7.3. Preferably, pH and/or other conditions will be maintained to optimize glucose metabolism by the cells while animal cells while reducing the production of lactic acid in the culture. The pH of a cell culture can be controlled by any suitable method, preferably in a manner that does not substantially inhibit the production of the adenoviral vector stock. Several suitable techniques for modifying pH are known in the art, including the addition of buffers (e.g., bicarbonate or tris buffers). Temperature is another factor that influences the production of the adenoviral vector stock after infection. Any temperature suitable for the production of the adenoviral vector stock can be utilized, preferably a temperature of about 35–40° C., more preferably about 36–38° C. (e.g., about 37° C.). Proper mixing of the culture is another condition which can be important to cell growth and adenoviral vector production. Other factors which may be considered include oxygen concentration, $CO_2$ perfusion rate, concentration, settling and flow rates of cells in the culture, and levels of particular nutrients and/or intermediates that impact cell growth and metabolism rates (e.g., glutamine) (see, e.g., Ho et al., *CRC Critical Reviews in Biotechnology*, 4(2), 185–252 (1986); Kyung et al., *Cytotechnology*, 14, 183–90 (1994); Yoon et al., *Biotechnology and Bioengineering*, 44, 983–990 (1994); and Oeggerli et al., *Biotechnology and Bioengineering*, 45, 54–62 (1995)). The aforementioned principles and techniques, though discussed in the context of post-infection culturing of the culture, are also applicable to pre-infection culture of the culture described herein.

While not wishing to be bound by any particular theory, it is believed that practice of the present invention impacts the dynamics of the cell cycle in the culture, resulting in improved adenoviral vector production by the culture. The dynamics of the cell cycle are characterized in, for example, Alberts et al., *Molecular Biology of the Cell* (2d ed. 1989). Specifically, in the context of the present invention, it is thought that when the cells in the culture reach a cell density of about 40–70% of the stationary phase density, the culture is in a state where nutrient levels are high enough to maintain high percentages of viable cells in the culture (e.g., above 85% or higher), but are low enough to cause a substantial number of the cells in the culture to undergo a $G_1$ suppression. During $G_1$ suppression, the normal cell cycle is suspended, and the culture becomes essentially a synchronous culture (i.e., a substantial portion of the cells in the culture enter the cell cycle at the same time and undergo stages of growth at similar times and rates). Synchronous cultures are advantageous for the production of products by cell culture, including viral vectors. This method of obtaining a synchronous culture is distinguishable from other techniques currently practiced (e.g., obtaining a synchronous culture through contacting the cells with chemical agents or by infection with some RNA-based viruses). It is further believed that, through the intense perfusion and accompanying medium replacement, the nutrients in the fresh medium enable the cells to overcome the $G_1$ suppression and provide a synchronous culture during and after infection with the adenoviral vectors. This belief is founded on, for example, the observation that post-infection medium exchange, within the ranges provided herein, is associated with a short and unusually rapid growth in the population of cells in the culture before such rates decline to predictable growth levels. Other methods known in the art can be used to ensure the culture is a synchronous culture, if desired. However, the use of such techniques are not desirable if they involve other viruses or if the synchronizing agents are harmful to the cells.

While the cells can be cultured by any method suitable for production of adenoviral vectors in infected cells under the aforementioned conditions, it is preferred that the infected cell culture is cultured in a bioreactor (also sometimes referred to as a fermentor) to produce large scale adenoviral vector stocks. Any suitable bioreactor can be used, which ensures proper mixing and preferably optimal pH and temperature conditions for culturing the culture, and which enables the perfusion of fresh medium through the culture in an amount equal to at least about two times the volume of the culture prior to infection. Examples of suitable bioreactors include stirred tank bioreactors, bubble column bioreactors, air lift bioreactors, fluid bed bioreactors, packed bed bioreactors, wave bioreactors, and flocculated cell bioreactors. Preferably, the bioreactor is not a microprojectile-based bioreactor. Desirably, the bioreactor is a stirred tank bioreactor, which prevents cell damage by shearing and turbulence during culture. The bioreactor can be either a batch, continuous, or fed-batch bioreactor, with perfusion capabilities, and the culture preferably is maintained under batch, fed-batch, or continuous culture conditions with the exception of the perfusion of fresh culture through the medium prior to infection at a volume equal to at least about two times the volume of the medium prior to infection with the adenoviral vectors. Preferably perfusion culture-capable bioreactors are used with variable volume fed-batch procedures (also referred to in the art as repeated fed-batch process or cyclic fed-batch culture) or batch procedures during the culturing of the cells prior to, and after, the perfusion of fresh medium through the culture. After such perfusion and infection, batch conditions are preferably maintained until harvest. Alternatively, continuous-perfusion cell culture conditions can be used in place of batch conditions during the initial growth of the cells and/or after infection, preferably where perfusion of fresh medium through the culture occurs in an amount significantly lower than the perfusion of at least two times the volume of medium in the culture performed prior to contact of the culture with the adenoviral vectors.

A bioreactor can be any suitable size for producing an appropriate size adenoviral vector stock. For large scale production, commercial 10 liter bioreactors, or larger bioreactors, are preferred. In aspects of the invention where roller bottles or other culture techniques are used prior to or during infection, cells can be transferred to the bioreactor by any appropriate techniques, such as a peristaltic pump.

After culturing the infected cells, the cells are harvested, and the adenoviral vector stock is produced. Any method of harvesting cells which will result in the recovery of adenoviral vectors can be used in the context of the present invention, and several technique for harvesting cells are known in the art, such as mechanical/physical and chemical techniques. In chemical harvesting, chemicals, usually detergents, are added to the culture to lyse the cells and release cellular components and the adenoviral vectors. Chemical techniques include the use of cell lysis solutions or lysis buffers, examples of which are Triton X-100 in PBS solution, Tris-HCl based lysing solutions, and polysorbate 80/Bicaine buffers. Physical techniques include the standard "freeze-thaw" method, wherein cells are treated with phosphate buffered saline, incubated in a $Ca^{2+}$ and $Mg^{2+}$-free buffered salt solution (such as TEN (40 mM Tris-HCl, pH 7.5, 1 mM EDTA, 150 mM NaCl)), pelleted, resuspended in Tris buffer, and then subjected to three freeze/thaw cycles to lyse cell membranes. Other freeze-thaw methods utilize protease inhibitors prior to performing freeze-thaw cycles, for example leupeptin, pepstatin, and phenylmethylsulfonyl fluoride (PMSF). Mechanical techniques include, for example, continuous centrifugation, French press, mill, crossflow filtration, and sonication methods (preferably performed in combination with crossflow filtration). Preferably chemical techniques, if used, are combined with mechanical techniques. After harvest of the cells, preferably further steps are taken to separate the adenoviral vector from the lysed cell components. Examples of such steps include removing lipids (for example by Freon addition, centrifugation, and removal of the aqueous phase containing the adenoviral vectors), tangential flow diafiltration to remove cellular debris, and removal of soluble antigens by performing chromatography-based separation, such as cesium chloride chromatography. Preferably, the method includes multiple chromatography steps, including a capture column, a purification column, and a size exclusion/buffer exchange column. Numerous other examples of such techniques, and modifications thereof, are known in the art, and the ordinarily skilled artisan will readily be able to select appropriate techniques for harvesting the adenoviral vectors.

Harvesting the cells can be done at any suitable time for deriving the desired stock of adenoviral vectors. Preferably, a harvesting time is selected that ensures optimal production of adenoviral vectors in the stock, balanced against efficiency of production by the cells in the culture. An ordinary artisan can readily make such determinations. Typically, harvest will occur at about 24–48 hours, or longer, post-infection (h.p.i.), and preferably harvest will occur between about 24 hours and 48 hours post-infection.

The quality of adenoviral vector stock production is dependent upon the viability of the cells at the time of infection. Accordingly, the culture desirably is contacted with the adenoviral vectors when the percentage of viable cells in the culture is such that a loss in the percentage of viable cells of 10% would result in an about 80% or more loss in focus forming units per cell (FFU/cell) when the cells are harvested. Similarly, the culture desirably is contacted with the adenoviral vectors when the percentage of viable cells in the culture is such that a loss in the percentage of viable cells of 20% would result in an about 90% or more loss in FFU/cell when the cells are harvested.

Preferably, the percentage of viable cells in the culture prior to infection (particularly, during and immediately after the intense perfusion) is maintained at about 75% or more of the total cells in the culture. More preferably, the percentage of viable cells in the culture prior to infection is about 80% or higher, more preferably about 85% or higher. Typically, in large cultures, the maximum sustainable percentages of viable cells in the culture will be about 95%. The viability of cells can be monitored and/or determined by any appropriate technique, including those discussed elsewhere herein.

Alternatively, or in addition, the culture can be contacted with the adenoviral vectors when the percentage of viable cells in the culture is such that a loss in the percentage of viable cells of 10% would result in an about 80% or more increase in the ratio of adenoviral particle units (PU) (total viral vector particles) per cell to focus forming units (FFU) or plaque forming units (PFU) per cell at harvest. PU can be determined by total viral titer techniques or other techniques suitable for determining the total number of viral vector particles. FFU represents the number of focuses formed by infected cells and is determined by means of an optical microscope using standard protocols. PFU can be determined by standard plaque assays, for example, by dyeing infected cells fixed with formalin with methylene blue solution. Other (immuno)histochemical staining solutions and fixing techniques also can be used. The ratio of PU/FFU is an important indicator of the efficiency of the production of active viral vectors. Lower ratios of PU/FFU indicate high ratios of active vectors to total vector production, indicating that the energy placed into vector production efficiently results in stocks of active vectors. Preferably, PU/FFU is about 100 or less, more preferably about 80 or less (e.g., 70 or less), even more preferably about 60 or less.

The determination of when a loss in the active adenoviral vectors at harvest will occur due to such drops in the percentage of cell viability at the time of infection can be determined by studying a sample culture or previous culture performed under substantially similar conditions to determine the point where the culture should be contacted with the adenoviral vectors. The percentage of active adenoviral vector can be determined by any appropriate techniques. Examples of such techniques include standard plaque assays. When the adenoviral vector is an adenoviral gene transfer vector, assays directed to the expression or presence of the exogenous gene can be used to determine the percentage of active adenoviral vectors. Total viral titer can be measured by any method known to those of skill in the art, examples of which are set forth in U.S. Pat. Nos. 4,861,719 and 4,868,116.

EXAMPLES

The following examples further illustrate the present invention, but, of course, should not be construed as in any way limiting its scope.

Example 1

This example demonstrates the volumetric yields of adenoviral vectors obtainable when cultures are infected with adenoviral vectors at various cell densities.

PER.C6 cells (Introgene, Inc.) were cultured in Ex-Cell 525 (JRH Biosciences, Inc.) with 4 mM glutamine added to the culture. Two liters of PER.C6 cell culture was seeded into a 3.5 liter bioreactor at $5\times10^5$ cells/ml with an average percentage of cell viability of over 90% at day 0. 750 ml of fresh medium was fed into the bioreactor on day 1 and day 2. On day 3, the culture was transferred to a 10 liter bioreactor with the addition of 6.5 liters of fresh medium. Stationary phase for a similar culture was estimated to coincide with a cell density of about $1.6\times10^6$ cells/ml. 300 ml samples of the cell culture were taken at various densities ranging from under $6\times10^5$ cells/ml to over $1\times10^6$ cells/ml (from less than 37% to more than 62% of the density of the culture at stationary phase).

Each sample was centrifuged at 1000 rpm for 5 minutes. Spent media was removed, and cells were resuspended with 30 ml fresh media. The percentage of viable cells in each sample was determined to range between 89 and 95%. The cells were then contacted with serotype 5-based adenoviral vectors (MOI=5) for one hour at 37° C. After one hour incubation, cells were resuspended in fresh media to a final volume of 300 ml for each sample. Each sample was divided into 100 ml sub-samples, and each sub-sample was cultured in a roller bottle culture at 37° C. At 48 hours post infection, cells were harvested, and PU/ml, PU/cell, and FU/ml were determined, and average PU/FFU ratios (and up to 1 standard deviation (s.d.) below or above the average) were calculated. Analyzed cultures were categorized into eight groups based on the percentage of the culture's stationary phase cell density in the culture at the time of infection (<38%, 38–43%, 44–49%, 50–55%, 56–62%, 63%, 75%, and 100%). Experiments were repeated 20 times at <38%, 63%, 75%, and 100% of the cell density at stationary phase, 23 times at 44–49%, 50–55%, and 56–62% of the cell density at stationary phase, and 48 times at 37–43% of the cell density at stationary phase. The results are presented in Table 1.

under about 40%, more particularly below about 38%, of the stationary phase cell density also showed a PU/FFU of about 120, essential double or higher than PU/FFU ratios achieved at cultures infected at higher densities. Cultures infected when cell density was over 70%, more particularly at 75%, of the stationary phase density resulted in significantly lower production of FFU/cell and PU/cell compared to cultures infected at about 70% or less, more particularly 63%, of the stationary phase cell density (a 75% and 73% decrease, respectively). These results indicate that cultures infected at densities less than 40%, more particularly less than 38%, or more than about 70%, more particularly at, or more than, about 75%, of the stationary phase cell density, show a significant reduction in their capacity to produce adenoviral vectors compared to cultures infected when cell density is at about 40–70% of the stationary phase density.

Yields of FFU/cell were highest in cultures infected at about 50–55% of the stationary phase cell density, but generally remained at high levels (i.e., about 600 or greater) in all cultures infected at about 40–70%, particularly 44–63%, of the stationary phase density (i.e., above 440). Lower FFU/cell yields in cultures infected at percentages of stationary phase density above 40% of the stationary phase, particularly within the 44–49% range and the 50–55% range, but at, or below, about 70%, particularly 63%, of the stationary phase density, were offset by the increased numbers of cells producing focus forming units in such cultures. For example, multiplying the FFU/cell for cultures within this range by the median percentage of the stationary phase density (e.g., 0.47 for the range 44–49%) provides an indication of the number of focus forming units produced at a given cell density. The number of focus forming units produced for cultures infected at about 60–70%, more particularly 63%, of the stationary phase density is approximately equal to the number produced in cultures infected at

TABLE 1

Adenoviral Vector Production in Cultures Infected at Varying Cell Densities

Average Percent of Cell Density at Stationary Phase at Time of Infection

|  | <38 | 38–43 | 44–49 | 50–55 | 56–62 | 63 | 75 | 100 |
|---|---|---|---|---|---|---|---|---|
| Avg. PU/ml | $1.90 \times 10^9$ | $1.5 \times 10^{10}$ | $1.8 \times 10^{10}$ | $2.0 \times 10^{10}$ | $2.5 \times 10^{10}$ | $3.7 \times 10^{10}$ | $1.1 \times 10^{10}$ | $1.9 \times 10^{10}$ |
| Avg. PU/cell | $0.45 \times 10^4$ | $2.3 \times 10^4$ | $2.4 \times 10^4$ | $2.3 \times 10^4$ | $2.7 \times 10^4$ | $3.6 \times 10^4$ | $0.96 \times 10^4$ | $1.2 \times 10^4$ |
| Avg. FFU/cell | 37 | 609 | 704 | 636 | 442 | 521 | 128 | 282 |
| Avg. PU/FFU +− 1 s.d. | 120 +/− 7 | 56 +/− 23 | 52 +/− 33 | 54 +/− 42 | 60 +/− 1 | 61 +/− 16 | 80 +/− 21 | 41 +/− 4 |

These results of the experiments, reflected in Table 1, demonstrate that infection with adenoviral vectors when cell density of the culture is about 60–70%, more particularly 63%, of the cell density at the stationary phase resulted in the highest levels of PU/ml and PU/cell, while the highest levels of FFU/cell were obtained in cultures infected at about 50–55% of the stationary phase cell density. Cultures infected with adenoviral vectors when cell densities were below 40%, more particularly below 38%, of the density at the stationary phase showed much lower yields of focus forming units and particle units per cell (e.g., only 7.1% and 12.1% of the levels obtained for cultures infected when density was 63% of the stationary phase density, respectively). Cultures infected when the cell density was about 40–50%, more particularly 44–49%, of the stationary phase cell density (FFU/cell×percent stationary phase cell density of 328 to 330, respectively). Moreover, the number of focus forming units per cell for cultures infected at about 40–70%, more particularly at 44% and 63%, of the stationary phase density, are 442 or higher, as compared to 37 for cultures infected at below 38% of the stationary phase density, and 128 for cultures infected at 75% stationary phase cell density (a 92% and 71% decrease, respectively). The results of these calculations demonstrate the effectiveness of cultures infected at about 40–70%, more particularly at 44–63%, of the stationary phase density to produce viable adenoviral vectors compared to cultures infected at cell densities above and below this range.

While PU/FFU ratios for cultures with cell density above 40%, particularly 44%, of the stationary phase density to about 70%, particularly 63%, of the stationary phase density were relatively stable (between 52 and 61), yields of particle units per cell and per milliliter were somewhat higher in cultures infected when cell density was nearer about 70%, particularly 63%, of the stationary phase cell density, as was total production of focus forming units. Later experiments, which were performed with cultures infected with adenoviral vectors at 65%, and for cultures infected with adenoviral vectors at 69%, of the stationary phase density, showed similar yields of PU/FFU to those observed with cultures infected at 63% of the stationary phase density. These results demonstrate that improved yields of adenoviral vectors are obtained when cells are infected at a time when cell density within the culture is within the percentages of the culture's stationary phase density provided by the present invention.

Example 2

This example demonstrates the effect of the percentage of viable cells in the culture at infection on adenoviral vector production.

PER.C6 cells were cultured in Ex-Cell 525 animal protein-free medium with 4 mM glutamine in roller bottles. Cell viability was determined during each run. The cells were permitted to grow to an approximate cell density of $1 \times 10^6$ cells/ml and percentage of viable cells of about 90%. The cells were centrifuged at 1000 rpm for 5 minutes, and spent medium was removed. Cultures were then resuspended in differing amounts of spent medium in order to obtain various viabilities by "starving" the cultures. Cell viability was then assessed. Cultures were contacted with serotype 5 adenoviral vectors under conditions permissive for infection for a period of one hour in cultures having various percentages of viable cells. The maximum percentage of viable cells in any of the cultures was approximately 95%. The cells were then harvested and adenoviral vectors were purified by chromatography. Assays were performed to determine particle units and focus forming units produced in the various cultures. Analyzed cells were categorized into six groups based on the percentage of viable cells in the culture at infection (i.e., 70–74%, 75–79%, 80–84%, 85–90%, and greater than 90% percent viable cells). The average ratio of particle units to focus forming units for each category is presented in Table 2a.

TABLE 2A

Effect of Cell Viability at Time of Infection on Ratio of Adenoviral Vector Particle Units/Focus Forming Units Obtained at Cell Harvest

| | Percentage of Viable Cells at Time of Infection | | | | |
|---|---|---|---|---|---|
| | >90 | 85–90 | 80–84 | 75–79 | 70–74 |
| PU/FFU | 36 | 45 | 37 | 55 | 286 |

These experiments were repeated except that in the second set of experiments analyzed cells were categorized into eight groups instead of six. Specifically, cells were infected when the percentage of viable cells was 60–64% and 65–69%, as well as at the other percentages of viable cells listed above. The results of this second set of experiments are set out in Table 2b.

TABLE 2B

Effect of Cell Viability at Time of Infection on Ratio of Adenoviral Vector Particle Units/Focus Forming Units Obtained at Cell Harvest

| | Percentage of Viable Cells at Time of Infection | | | | | | |
|---|---|---|---|---|---|---|---|
| | >90 | 85–90 | 80–84 | 75–79 | 70–74 | 65–69 | 60–64 |
| Average PU/FFU | 49 | 38 | 49 | 58 | 99 | 78 | 105 |

As can be seen in Tables 2a and 2b, infecting the culture with the adenoviral vectors when the percentage of viable cells in the culture was 70–74% or lower resulted in significant increases in the PU/FFU ratio for such cultures. For example, the average increase in PU/FFU for cultures measured in the second set of experiments (the results of which are set forth in Table 2b), was 74% from cultures infected when the percentage of viable cells in the culture was between 75 and 79%, whereas for cultures in the first set of experiments the change in PU/FFU from cultures infected when the percentage of viable cells was 75–79% compared to 70–74% was over a 500% increase. In contrast, PU/FFU ranges for cultures infected when the percentage of viable cells in the culture was over 75% remained relatively constant (55–36). Average FFU/cell also significantly decreased in cultures with lower percentages of viable cells. Specifically, for the experiments reflected in Table 2a, average FFU/cell in cultures infected with 70–74% viable cells in the culture was only 4.3 compared to 22, 60, 244, and 716 for the other cultures, respectively (over an 80% drop in FFU/cell for cultures infected when the percentage of viable cells was 75–59% and over 90% drop from cultures infected when the percentage was 80–84%). These results demonstrate that the present invention provides a method of efficiently producing viral vector stocks.

Example 3

This example demonstrates the effect of fresh medium availability in the culture on the production of adenoviral vectors.

PER.C6 cells were cultured in roller bottles at a volume of 100 ml/roller bottle, centrifuged to $\frac{1}{10}$th original volume, and infected with adenoviral vectors (serotype 5-based adenoviral gene transfer vectors) under conditions permissive for infection for one hour (MOI=5). Infection was done in a 50% fresh medium/50% spent medium mixture for one hour. After infection, cells were resuspended in 100% fresh medium, 100% spent medium or a mixed medium of 90%, 70%, 50% or 30% fresh medium to the original volume. The cells were cultured and harvested 48 h.p.i., and PU/ml was determined. Experiments were performed in triplicate, except for the instance when 30% fresh medium was added. The results of these experiments are set forth in Table 3.

TABLE 3

Effect of Medium Exchange on Adenoviral Vector Particle Unit Production

| | Percentage of fresh medium added post infection | | | | | |
|---|---|---|---|---|---|---|
| | 100 | 90 | 70 | 50 | 30 | 0 |
| Avg. PU/ml | $1.0 \times 10^{10}$ | $1.0 \times 10^{10}$ | $8.5 \times 10^9$ | $6.9 \times 10^9$ | $4.9 \times 10^9$ | $2.6 \times 10^9$ |

As shown in Table 3, post infection medium exchange significantly impacts the production of particle units in cultures at harvest. On average, there was no significant change in adding 90% versus 100% fresh medium. The addition of 70% fresh medium post-infection resulted in a yield of approximately 85% of the PU/ml obtained with the addition of 100% fresh medium. The addition of 50% fresh medium post-infection resulted in a yield of approximately 69% of the PU/ml obtained with the addition of 100% fresh medium. At lower percentages of fresh medium added, the PU/ml values dropped significantly compared to 100% fresh medium added. For example, when no fresh medium was added, only about ¼th of the PU/ml was obtained as compared to the PU/ml for 100% fresh medium added.

The results of this experiment demonstrate that higher yields of adenoviral vectors can be obtained with higher concentrations of fresh medium in the culture, in accordance with the present invention.

All references, including publications, patent applications and patents, cited herein are hereby incorporated by reference to the same extent as if each reference were individually and specifically indicated to be incorporated by reference and were set forth in its entirety herein. The use of the terms "a" and "an" and "the" and similar referents in the context of describing the present invention (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., "such as") provided herein, is intended merely to better illuminate the present invention and does not pose a limitation on the scope of the claimed invention. No language in the specification should be construed as indicating any non-claimed element as essential to the practice of the invention.

The foregoing is an integrated description of the invention as a whole, not merely of any particular element or facet thereof. The description describes "preferred embodiments" of this invention, including the best mode known to the inventors for carrying it out. Of course, upon reading the foregoing description, variations of those preferred embodiments will become obvious to those of ordinary skill in the art. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is possible unless otherwise indicated herein or otherwise clearly contradicted by context.

What is claimed is:

1. A method of producing an adenoviral vector stock comprising:
   (a) providing a culture of cells permissive for growth of adenoviral vectors, wherein the cells are in a medium,
   (b) culturing the culture under conditions to permit growth of the cells,
   (c) perfusing fresh medium through the culture for a period of about 1–6 hours, in an amount of at least about two times the volume of medium in the culture, while the density of the cells in the medium is about 40–70% of the density of cells obtained in the medium when the growth of the culture is in the stationary phase,
   (d) contacting the culture with adenoviral vectors under conditions permissive for the infection of the cells,
   (e) culturing the infected cells to replicate the adenoviral vectors, and
   (f) harvesting the infected cells to obtain an adenoviral vector stock.

2. The method of claim 1, wherein the culture is not concentrated before perfusion of the fresh medium or during the contact of the culture with the adenoviral vectors.

3. The method of claim 1, wherein the culture before and after the perfusion of fresh medium in step (c) is cultured under batch or fed-batch conditions.

4. The method of claim 3, wherein no medium is added to the culture, or exchanged, after the perfusion of fresh medium in step (c) is completed.

5. The method of claim 1, wherein the fresh medium in an amount of at least about two times the volume of medium in the culture is perfused through the culture while the density of cells in the medium is about 60–70% of the density of cells obtained in the medium when the growth of the culture is in the stationary phase.

6. The method of claim 1, wherein the ratio of adenoviral particle units to adenoviral focus forming units produced at harvest of the cells is about 70 or less.

7. The method of claim 1, wherein the fresh medium in an amount of about three to four times the volume of medium in the culture is perfused through the culture while the density of cells in the medium is about 40–70% of the density of cells obtained in the medium when the growth of the culture is in the stationary phase.

8. The method of claim 1, wherein the cells are grown in a non-microcarrier containing suspension culture.

9. The method of claim 1, wherein the adenoviral vectors are replication deficient adenoviral vectors.

10. The method of claim 1, wherein the cells are either human embryonic kidney cells, human embryonic lung cells, or human embryonic retinoblast cells.

11. The method of claim 10, wherein the cells are 293 cells, A549 cells, PER.C6 cells, 911 cells, or cells of cell lines derived therefrom.

12. The method of claim 10, wherein the cells are cultured, prior to infection with the adenoviral vectors, under batch or fed-batch conditions, fresh medium is perfused through the culture in an amount of about three to four times the volume of medium in the culture while the density of cells in the medium is about 50–65% of the density of cells obtained in the medium when the growth of the culture is in the stationary phase, the cells are contacted with the adenoviral vectors without concentrating the culture under conditions permissive for the infection of the cells and after the perfusion of fresh medium in step (c) is completed and when the percentage of viable cells in the medium is about 75% or more, and culturing the infected cells under batch conditions without the addition of fresh medium to replicate the adenoviral vectors, whereby the ratio of adenoviral particle units to adenoviral focus forming units produced at harvest of the cells is about 70 or less.

13. The method of claim 1, wherein the density of cells in the medium at stationary phase is about $1.5–9 \times 10^6$ cells/ml.

14. The method of claim 1, wherein the density of cells in the medium at time of infection is about $0.8–4.2 \times 10^6$ cells/ml.

15. The method of claim 1, wherein the method comprises replacing about 95% or more of the medium with fresh medium by the perfusion of medium through the culture.

16. The method of claim 1, wherein the method further comprises maintaining the pH of the medium at about 6.9–7.5 during and/or after contacting the culture with the adenoviral vectors.

17. The method of claim 1, wherein the culture is contacted with the adenoviral vectors when the percentage of viable cells in the medium is about 75% or more.

18. The method of claim 1, wherein the adenoviral vectors comprise adenoviral gene transfer vectors.

19. The method of claim 1, wherein the medium is an animal protein-free medium.

20. The method of claim 1, wherein the culture is contacted with the adenoviral vectors after the perfusion of fresh medium in step (c) is completed.

* * * * *